(12) United States Patent  
Kapadia (10) Patent No.: US 8,376,979 B2
(45) Date of Patent: Feb. 19, 2013

(54) METHOD AND APPARATUS OF A CARDIAC FLUID FLOW PATH

(75) Inventor: Samir R Kapadia, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1004 days.

(21) Appl. No.: 12/233,287

(22) Filed: Sep. 18, 2008

(65) Prior Publication Data

US 2009/0163847 A1 Jun. 25, 2009

Related U.S. Application Data

(60) Provisional application No. 60/974,897, filed on Sep. 25, 2007.

(51) Int. Cl.
*A61M 5/00* (2006.01)
(52) U.S. Cl. .................................. 604/8; 604/9
(58) Field of Classification Search ............... 604/8–10, 604/27–30, 500–510, 164.13; 623/1.11, 623/1.14, 1.15, 1.24; 600/16, 17
See application file for complete search history.

(56) References Cited

U.S. PATENT DOCUMENTS

| | | | |
|---|---|---|---|
| 6,155,264 | A | 12/2000 | Ressemann et al. |
| 6,299,637 | B1 | 10/2001 | Shaolian et al. |
| 7,011,095 | B2 | 3/2006 | Wolf et al. |
| 7,077,801 | B2 | 7/2006 | Haverich |
| 7,513,863 | B2 * | 4/2009 | Bolling et al. ............ 600/16 |
| 2002/0123786 | A1 | 9/2002 | Gittings et al. |
| 2003/0045828 | A1 * | 3/2003 | Wilk ........................ 604/8 |
| 2005/0043781 | A1 | 2/2005 | Foley |
| 2006/0142848 | A1 | 6/2006 | Gabbay |
| 2007/0010781 | A1 * | 1/2007 | Vijay ....................... 604/8 |

OTHER PUBLICATIONS

Cooley et al., "Left Ventricle to Abdominal Aorta Conduit for Relief of Aortic Stenosis", *Cardiovascular Diseases, Bulletin of the Texas Heat Institute*, 1975;2:376-383.
Chiappini et al., "Right Ventricular Outflow Tract Reconstruction with Contegra Monocuspid Transannular Patch in Tetralogy of Fallot", *Ann. Thorac. Surg.*, 2007;83:185-187.
McGoon, "Left Ventricular and Biventricular Extracardiac Conduits", *J. Thorac. Cardiovasc. Surg.*, 1976, 72:7-14.
Khambadkone et al., "Percutaneous Pulmonary Valve Implantation in Humans Results in 59 Consecutive Patients", *Circulation*, 2005, 112:1189-1197.

* cited by examiner

*Primary Examiner* — Philip R Wiest
(74) *Attorney, Agent, or Firm* — Tarolli, Sundheim, Covell & Tummino LLP (57) ABSTRACT

A method of placing a left ventricle outflow tract of a patient's heart into fluid communication with an ascending aorta through an artificial fluid flow path includes arranging a guidewire within a patient's body with a distal guidewire end in a left ventricle of the heart, a proximal guidewire end in the ascending aorta, and a guidewire body, extending longitudinally between the distal and proximal guidewire ends, located at least partially in a right atrium of the heart. A conduit is provided, the conduit having longitudinally spaced first and second conduit ends in mutual fluid communication through a tubular conduit body. The conduit is advanced along the guidewire from a chosen one of the proximal and distal guidewire ends toward the other one of the proximal and distal guidewire ends. The first conduit end is anchored in the left ventricle. The second conduit end is anchored in the ascending aorta to provide the artificial fluid flow path.

4 Claims, 11 Drawing Sheets

METHOD AND APPARATUS OF A CARDIAC FLUID FLOW PATH

RELATED APPLICATION

This application claims priority from U.S. provisional patent application Ser. No. 60/974,897, filed Sep. 25, 2007, the entirety of which is hereby incorporated by reference.

TECHNICAL FIELD

The present invention relates to an apparatus and method for use of a cardiac fluid flow path and, more particularly, to a method and apparatus of placing a left ventricle outflow tract ("LVOT") of a patient's heart into fluid communication with the patient's ascending aorta through an artificial fluid flow path.

BACKGROUND OF THE INVENTION

A reduction in a heart's cardiac output (i.e., the reduced ability of the heart to output oxygenated blood from the left side of the heart) may result from various abnormalities and diseases of the heart. This reduction in output may be due, for example, to aortic valve disease. There are two major categories of aortic heart valve disease: stenosis and regurgitation. Stenosis involves the narrowing of the aortic outflow tract, causing obstruction to blood flowing from the left ventricle into the ascending aorta. The stenosis typically involves the buildup of calcified material on the valve leaflets, causing them to thicken and impairing their ability to fully open to permit adequate forward blood flow. Stenotic build up may also occur beneath the valve leaflets (i.e., subvalvular stenosis). Severe calcification can greatly impair proper functioning of the aortic valve and obstruct blood outflow from the heart. Regurgitation, on the other hand, is the retrograde leakage of blood back through the heart valve and into the left ventricle during diastole. Both stenosis and regurgitation of the aortic valve lead to left ventricular hypertrophy to compensate for the valvular dysfunction. Ultimately, there is dilatation and failure of the left ventricle resulting in decrease cardiac output and increased filling pressure in the heart.

Surgical treatments are available to treat valve dysfunction; however, these treatments have drawbacks. For example, the most common treatment for stenotic aortic valves is the surgical replacement of the diseased valve, which can be very invasive, requiring dissection of the patient's aorta. A particular drawback of conventional aortic valve replacement procedures is that they require the patient to be placed on the heart-lung machine ("on-pump"), wherein the heart is stopped and the surgery is performed through the patient's open chest. Because the success of these procedures can only be determined when the heart is beating, the heart must be closed up and the patient taken off the heart-lung machine ("off-pump") before verification of surgical success can be made. If the off-pump results are determined to be inadequate, the patient must be put back on-pump and the aorta must be reopened. Moreover, the risks and complications associated with open-heart surgery—involving the use of cardiopulmonary bypass, aortic cross-clamping, and cardioplegic arrest—are well-known. The most serious risks of cardiopulmonary bypass and aortic cross-clamping are the increase in the likelihood of bleeding and stroke. Also, patients who undergo surgeries using cardiopulmonary bypass often require extended hospital stays and experience lengthy recoveries. Thus, while certain conventional heart surgeries produce beneficial results for many patients, numerous others who might benefit from such surgery are unable or unwilling to undergo the trauma and risks of conventional procedures.

Within recent years, minimally invasive types of procedures for coronary artery bypass surgery have been developed which do not require stopping the patient's heart and the use of cardiopulmonary bypass. While attempts have been made to treat aortic valves off-pump via endovascular procedures, such as endovascular balloon valvuloplasty, such procedures may provide only partial and temporary relief for a patient with a stenotic valve. Moreover, the rapid restenosis and high mortality following balloon aortic valvuloplasty have led to disfavor of this procedure in the field.

Even off-pump minimally invasive procedures currently used, such as endovascular aortic valve replacement, may include a risk of dislodgement of stenotic particles from the native aortic valve. Dislodged particles, or other debris released into the patient's cardiovascular system during surgery may travel to other parts of the patient's body and lead to obstructions and even strokes. Further, the delivery sheath requirement for the endovascular valves is large and many patients have peripheral vascular disease that precludes them from having this procedure. Therefore, a surgeon may desire to supplement blood flow through the patient's aortic valve without disturbing stenoses or other potentially obstructing material within the heart.

SUMMARY OF THE INVENTION

In an embodiment of the present invention, a method of placing a left ventricle outflow tract of a patient's heart into fluid communication with an ascending aorta through an artificial fluid-flow path is described. A guidewire is arranged within a patient's body with a distal guidewire end in a left ventricle of the heart, a proximal guidewire end in the ascending aorta, and a guidewire body, extending longitudinally between the distal and proximal guidewire ends, located at least partially in a right atrium of the heart. A conduit is provided, the conduit having longitudinally spaced first and second conduit ends in mutual fluid communication through a tubular conduit body. The conduit is advanced along the guidewire from a chosen one of the proximal and distal guidewire ends toward the other one of the proximal and distal guidewire ends. The first conduit end is anchored in the left ventricle. The second conduit end is anchored in the ascending aorta to provide the artificial fluid flow path.

In an embodiment of the present invention, an apparatus for placing a left ventricle outflow tract of a patient's heart into fluid communication with an ascending aorta through an artificial fluid flow path is described. Means for placing a conduit within the patient's body are provided. The conduit has longitudinally spaced first and second conduit ends in mutual fluid communication through a tubular conduit body. Means for anchoring the first conduit end in the left ventricle are provided. Means for anchoring the second conduit end in the ascending aorta to provide the artificial fluid flow path are provided.

In an embodiment of the present invention, a method of placing a left ventricle outflow tract of a patient's heart into fluid communication with an ascending aorta through an artificial fluid flow path is described. A distal first guidewire end is routed through a right atrium of the heart into a left ventricle of the heart. A distal second guidewire end is routed through the right atrium into the ascending aorta. The distal second guidewire end is advanced caudad to the patient. A proximal first guidewire end and a proximal second guidewire end are linked at a guidewire junction. The distal second guidewire end is externally accessed. A conduit is provided, the conduit having longitudinally spaced first and second conduit ends in mutual fluid communication through a tubular conduit body. The distal second guidewire end is introduced into the first conduit end. The conduit is advanced toward the guidewire junction. The conduit body is extended through the right atrium. The first conduit end is anchored in the left ventricle. The second conduit end is anchored in the ascending aorta to provide the artificial fluid flow path.

In an embodiment of the present invention, an apparatus for placing a left ventricle outflow tract of a patient's heart into fluid communication with an ascending aorta through an artificial fluid flow path is described. A first guidewire has distal and proximal first guidewire ends longitudinally spaced by a first guidewire body. The distal first guidewire end is located in a left ventricle of the heart. The first guidewire body extends through an atrioventricular septum of the heart. A second guidewire has distal and proximal second guidewire ends longitudinally spaced by a second guidewire body. The distal second guidewire end is located in an ascending aorta of the heart. The second guidewire body extends through a wall of the ascending aorta and into a right atrium of the heart. A conduit has longitudinally spaced first and second conduit ends in mutual fluid communication through a tubular conduit body. The first conduit end is adapted for anchoring in the left ventricle. The second conduit end is adapted for anchoring in the ascending aorta. The proximal first and second guidewire ends are selectively linked at a guidewire junction. The conduit is introduced to the heart by advancement from the distal second guidewire end. The conduit body extends through the right atrium when the conduit is anchored within the heart to provide the artificial fluid flow path.

BRIEF DESCRIPTION OF THE DRAWINGS

For a better understanding of the invention, reference may be made to the accompanying drawings, in which.

DESCRIPTION OF EMBODIMENTS

Figure 1:
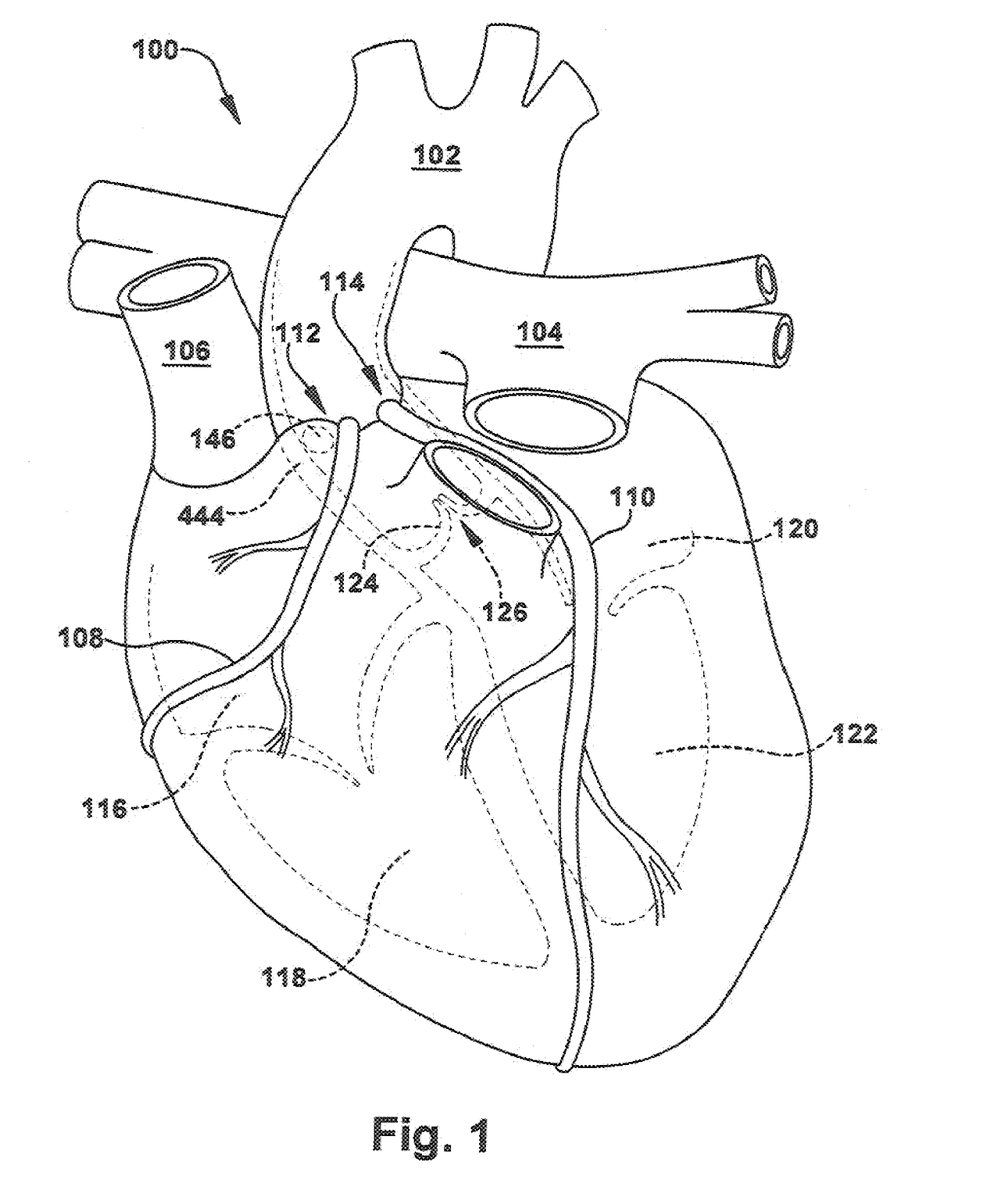
FIG. 1 is a schematic anterior view of a heart.

In accordance with the present invention, FIG. 1 depicts a heart 100. The heart 100 of FIG. 1 is a human heart, however, the present invention may be used with a non-human heart. In FIG. 1, three blood vessels are depicted as arising from an upper surface of the heart 100: the ascending aorta 102, pulmonary trunk 104, and superior vena cava 106. The right coronary artery 108 and left coronary artery 110 extend from the ascending aorta 102 at the right and left anterior aortic sinuses 112 and 114, respectively. FIG. 1 also includes several interior heart 100 features shown in phantom line: the right-atrium 116, right ventricle 118, left atrium 120, and left ventricle 122. A native aortic valve 124 connects the left ventricle 122 and the ascending aorta 102. A left ventricle outflow tract, shown generally at arrow 126, provides a fluid flow path for blood leaving the heart 100.

To supplement or bypass the natural left ventricle outflow tract 126, a surgeon may choose to provide a patient's heart 100 with an artificial fluid flow path. FIGS. 2-10, which are each a cutaway schematic anterior view of a heart, depict in sequence a method of, and apparatus for, placing a left ventricle outflow tract 126 of a heart 100 into fluid communication with an ascending aorta 102 through an artificial fluid flow path.

Figure 2:
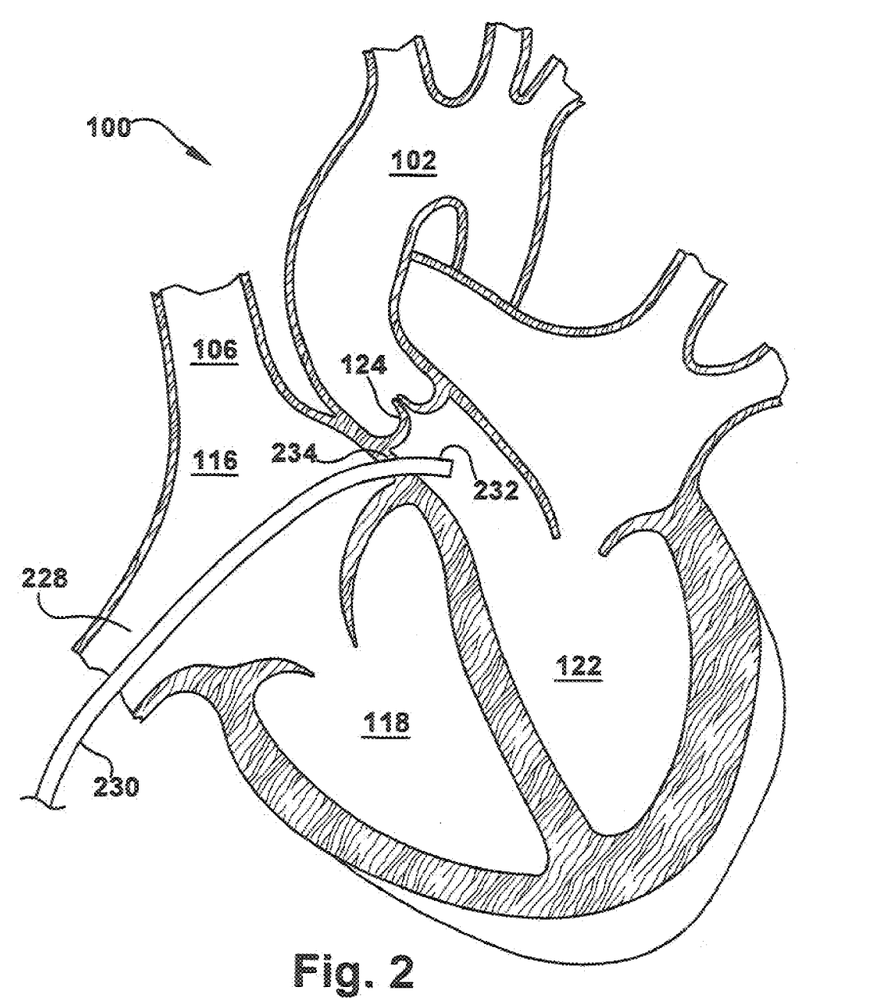
FIGS. 2-10 are cutaway schematic anterior views of a heart which depict a sequence of operation of an embodiment of the present invention.

In FIG. 2, the inferior vena cava 228 is the entry point for an introduction catheter 230 into the right atrium 116 of the heart 100. The introduction catheter 230 may enter the patient's body in any suitable manner, such as by percutaneous insertion via the Seldinger technique into a femoral artery (not shown). Once the introduction catheter 230 is threaded through the patient's vascular system into the inferior vena cava 228, a distal introduction catheter end 232 crosses the right atrium 116. The distal introduction catheter end 232 then punctures an atrioventricular septum 234 in a known manner to enter the left ventricle 122.

Figure 3:
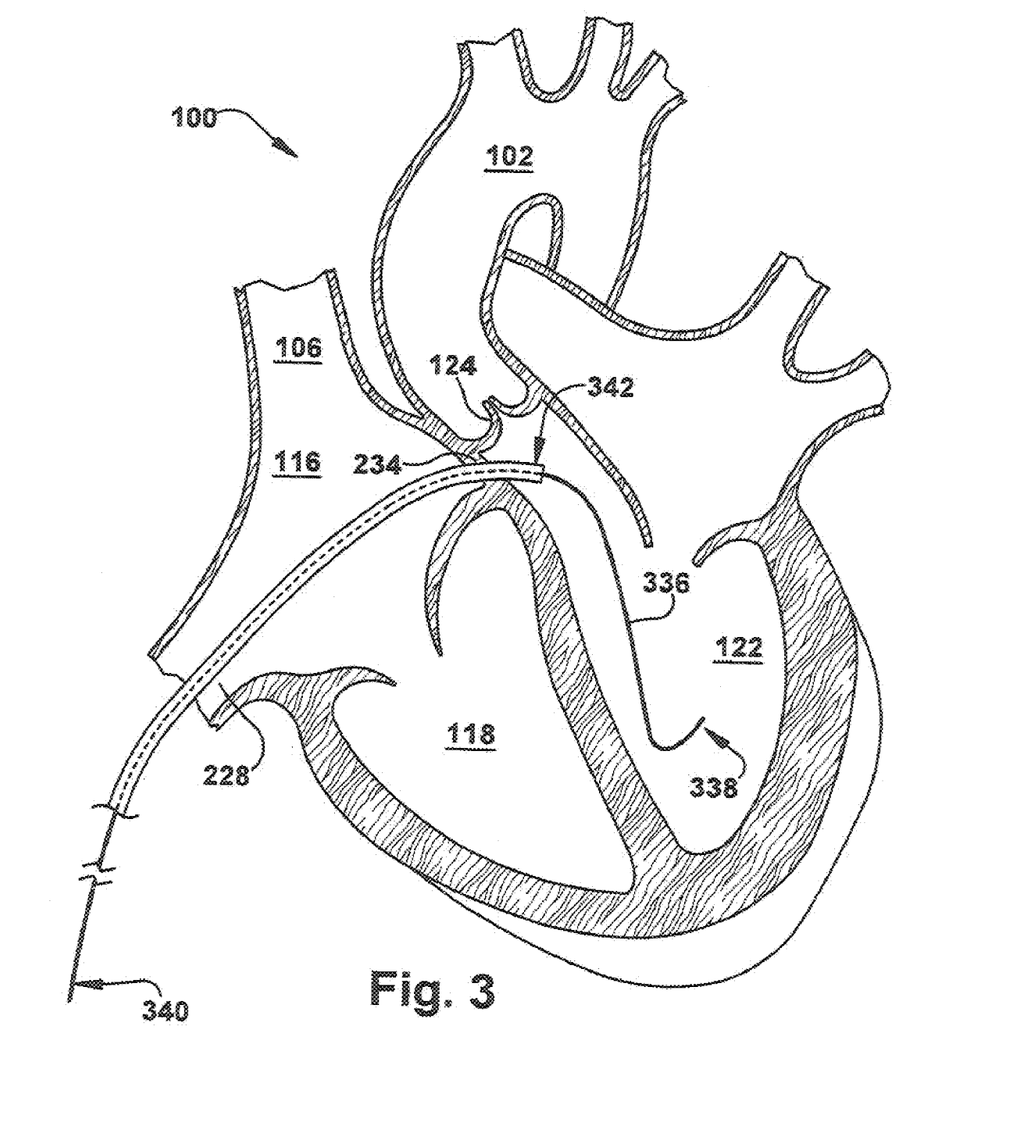

Once the distal introduction catheter end 232 is located in the left ventricle 122, a first guidewire 336 is passed into and through the introduction catheter 230 from outside the patient's body, as shown in FIG. 3. The first guidewire 336 has distal and proximal first guidewire ends 338 and 340, respectively, longitudinally spaced by a first guidewire body 342. The distal first guidewire end 338 is routed through the right atrium 116 and into the left ventricle 122, with the first guidewire body 342 extending through the atrioventricular septum 234. The proximal first guidewire end 340 may be located outside or within the patient's body, or may be later moved into or out of the patient's body, as may be suitable for use at any point during this procedure.

Figure 4:
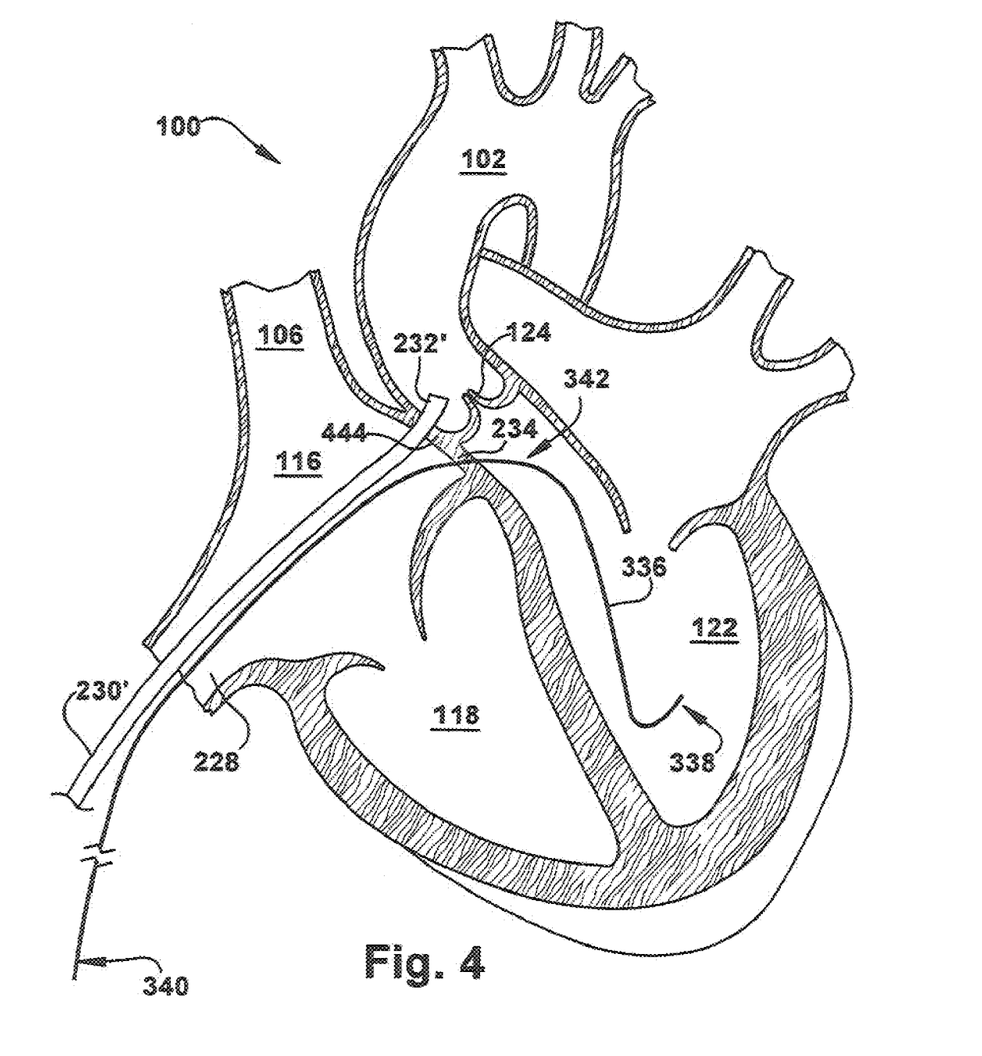

When the first guidewire 336 is positioned as desired within the heart 100, the introduction catheter 230 may be withdrawn from the heart 100 to leave the first guidewire 336 in position. Next, and as shown in FIG. 4, another introduction catheter 230' (which may be the same as, or different than, the introduction catheter 230 used to route the first guidewire 336) is threaded through the inferior vena cava 228 and crosses the right atrium 116. The distal introduction catheter end 232' then punctures a wall 444 of the ascending aorta 102 to enter the ascending aorta 102.

Returning briefly to FIG. 1, the wall 444 of the ascending aorta 102 may be punctured from within the right atrium 116 at an aortic access area 146 within the heart 100, as will be presumed in the below description. The aortic access area 146 is located posterior to the right coronary artery 108, as shown in FIG. 1 in the non-coronary cusp area.

Figure 5:
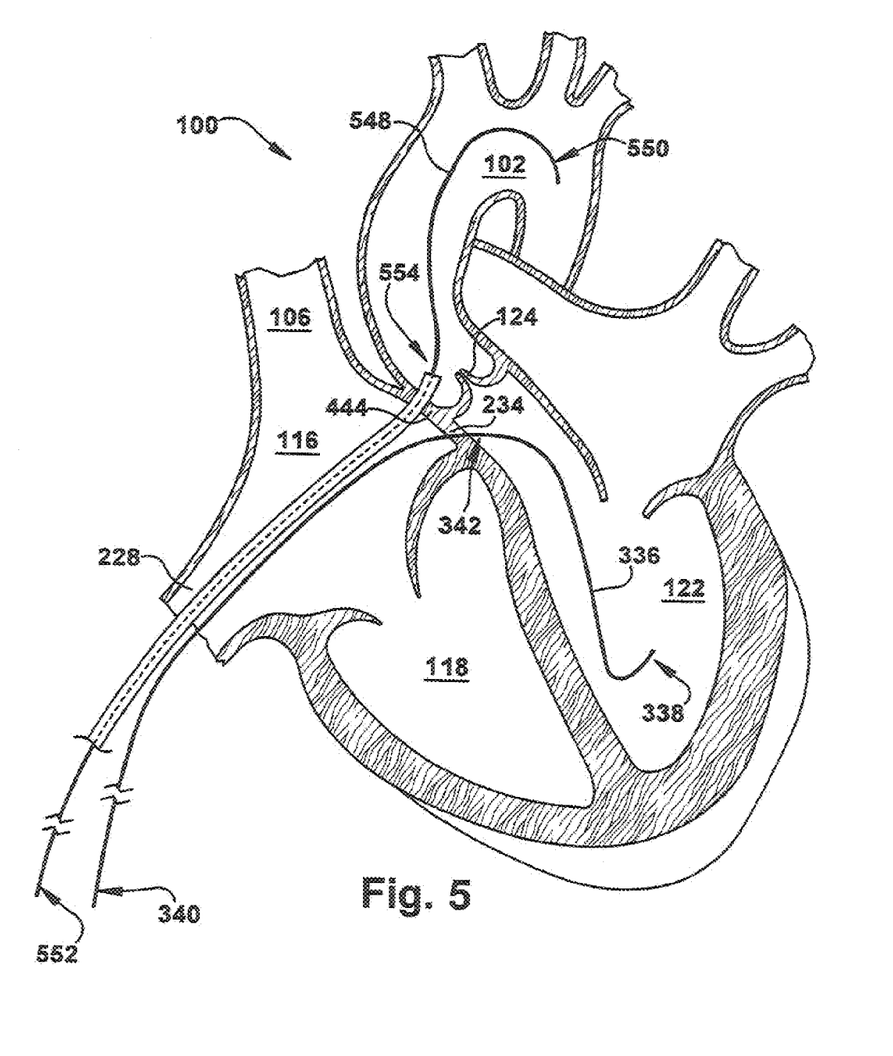

Turning now to FIG. 5, a second guidewire 548 is passed into and through the introduction catheter 230' from outside the patient's body. The second guidewire 548 has distal and proximal second guidewire ends 550 and 552, respectively, longitudinally spaced by a second guidewire body 554. The distal second guidewire end 550 is routed through the right atrium 116 and into the ascending aorta 102, with the second guidewire body 554 extending through the wall 444 of the ascending aorta. The proximal second guidewire end 552 may be located outside or within the patient's body, or may be later moved into or out of the patient's body, as may be suitable for use at any point during this procedure.

Figure 6:
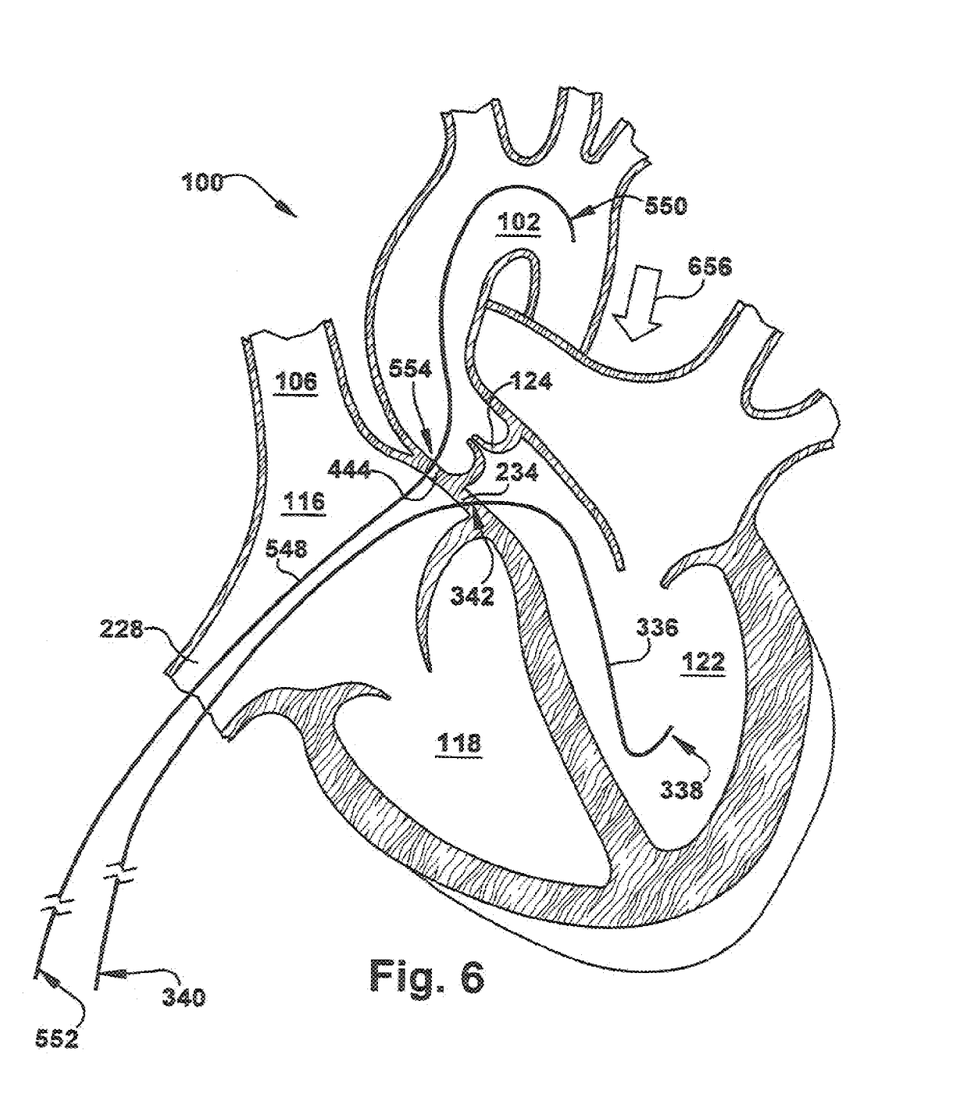

When the second guidewire 548 is positioned as desired within the heart 100, the introduction catheter 230' may be withdrawn from the heart 100 to leave the second guidewire 548 in position, as shown in FIG. 6. Though the first and second guidewires 336 and 548 were depicted in FIGS. 2-5 as being inserted in a certain manner and order, one of ordinary skill in the art could readily insert the first and/or second guidewires in any other suitable manner and/or order, with or without the assistance of any other guidewires or other structures (not shown), to achieve the configuration of FIG. 6.

Once the first and second guidewires 336 and 548 are positioned as shown in FIG. 6, the distal second guidewire end 550 is advanced caudad to the patient, in the direction of arrow 656. In subsequent Figures, the distal second guidewire end 550 will not be shown, but the following discussion presumes that the distal second guidewire end has passed through the ascending aorta 102 and to the descending aorta (not shown) or even further downstream from the heart 100 in the patient's cardiovascular system.

Figure 7:
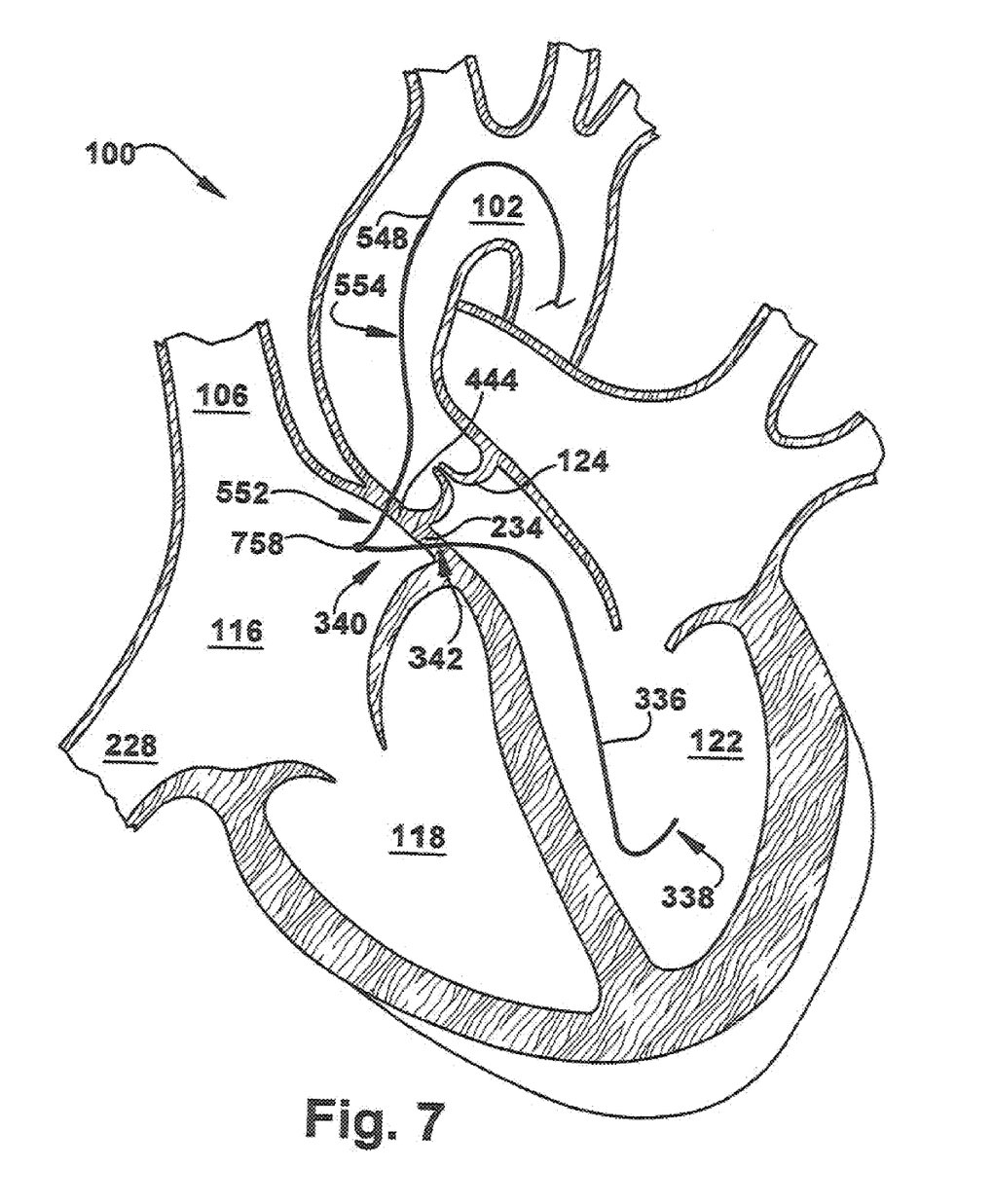

Either separately from, or in conjunction with, the advancement of the distal second guidewire end 550 in the caudad direction 656, the proximal first and second guidewire ends 340 and 552 may be linked at a guidewire junction 758, as shown in FIG. 7. The guidewire junction 758 is shown in the Figures, for greater visibility, as being an enlarged bead with the first and second guidewires 336 and 548 leading into the bead from the same direction, but may be of any suitable type, formed in any desired manner, and having any suitable relationship/orientation with the first and/or second guidewires. For example, the proximal first and second guidewire ends 340 and 552 may be adhered together with an additionally supplied adhesive, bonded through welding/soldering/etc., mechanically coupled with or without an additionally supplied structure/component, or the like. At the end of the linkage process, the first and second guidewires 336 and 548 will form a compound guidewire that functions as a single structure in at least a portion of the following steps.

Moreover, it is contemplated that one or both of the first and second guidewires 336 and 548 may be truncated during the process of linkage to form the guidewire junction 758. For example, the first guidewire body 342 could be severed, before or after formation of the guidewire junction 758, to reduce the total length of the first guidewire 336. The first guidewire 336 may be shortened to fit fully within the heart 100, as shown in FIG. 7, in this example. In the event that one or both of the first and second guidewires 336 and 548 is chosen for shortening concurrently with formation of the guidewire junction 758, or at any other time during operation of the present invention, the proximal-most end of the now-severed first or second guidewire 336 or 548 will be considered to be the proximal first or second guidewire end 340 and 552, respectively, after such severance is made. Similarly, if one or both of the first and second guidewires 336 and 548 is shortened from the distal end thereof, the distal-most end of the now-severed first or second guidewire 336 or 548 will be thereafter considered to be the distal first or second guidewire end 338 and 550, respectively. The proximal/distal nomenclature herein is not intended to limit the modification and/or rearrangement of any components of the present invention, but instead is merely used for clarity and ease of reference.

Figure 8:
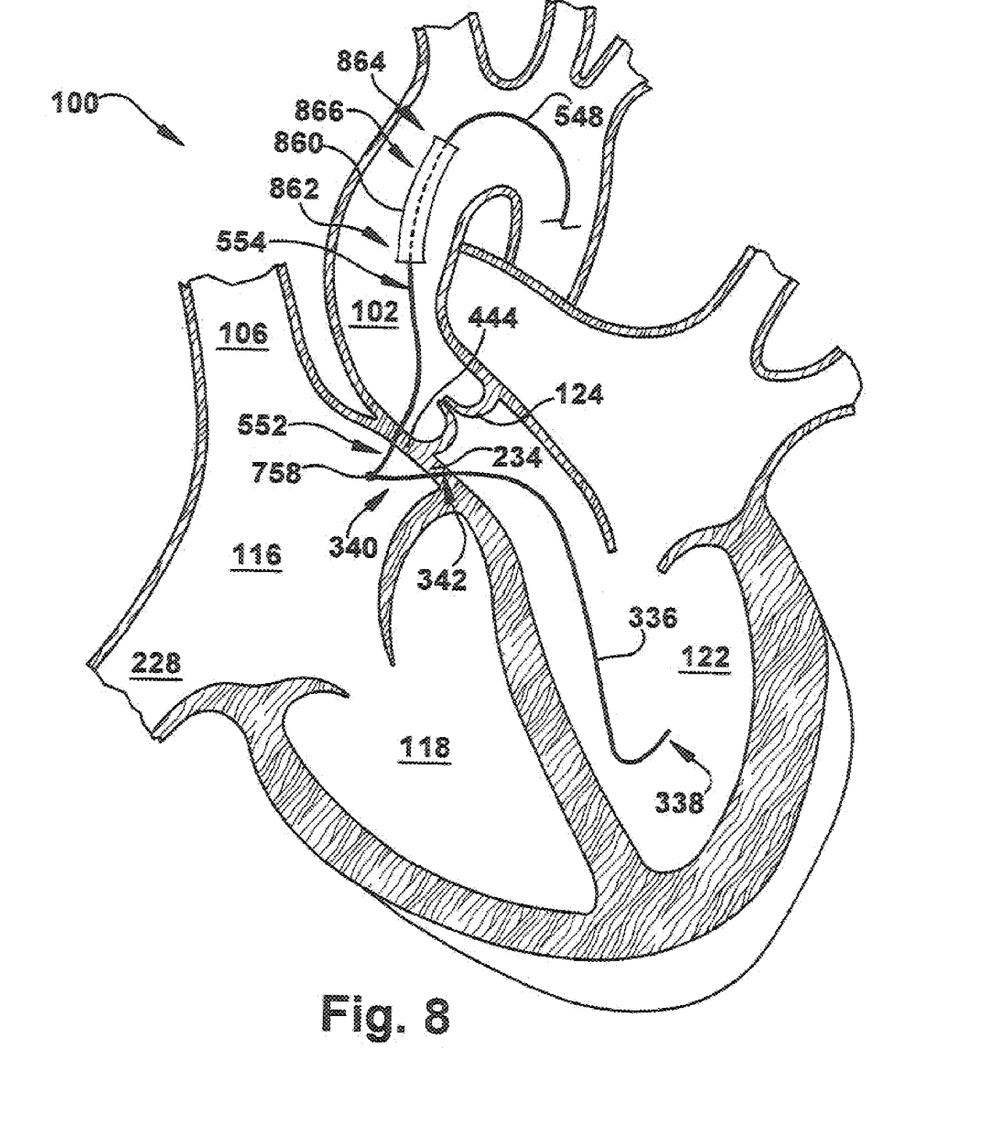

A conduit 860, as shown in FIG. 8, may be provided to facilitate the creation of the artificial fluid flow path. The conduit 860 has longitudinally spaced first and second conduit ends 862 and 864, respectively, in mutual fluid communication through a tubular conduit body 866. The conduit 860 may be of any suitable type, configuration, arrangement, size, shape, or the like, and may be made of any suitable natural or artificial material(s). The first and second conduit ends 862 and 864 are adapted for anchoring in the left ventricle 122 and ascending aorta 102, respectively. For example, one or both of the first and second conduit ends 862 and 864 may be flared, as shown in the Figures, to assist with anchoring in a desired manner. The conduit 860, or a portion thereof, may be compressible into a reduced-diameter configuration for travel to the heart 100, and then may be automatically or manually expanded from the reduced-diameter configuration once in a desired position within the heart 100.

After the first and second guidewires 336 and 548 are linked at the guidewire junction 758 into the arrangement shown in FIG. 7, the distal second guidewire end 550 may be accessed from outside the patient's body. This external access may be done in any suitable manner. For example, the distal second guidewire end 550 may be routed to a predetermined location, such as a catheter port, through which the distal second guidewire end may protrude from the patient's body. Steering of a guidewire within the patient's complex vascular system may be difficult, however, so it may be desirable for the distal second guidewire end 550 to be retrieved while within the patient's body. For example, the distal second guidewire end 550 could be snared with a third guidewire (not shown) in a known manner, the third guidewire being introduced into the patient via any suitable path, such as through a femoral artery (not shown).

After the distal second guidewire end 550 becomes accessible from outside the patient, the conduit 860 may be threaded onto the second guidewire 548 and introduced into the heart 100. As shown in the orientation of FIG. 8, this may be accomplished by introducing the distal second guidewire end 550 into the first conduit end 862. The conduit 860 can then be advanced over the second guidewire body 554 toward the guidewire junction 758, passing through the position shown in FIG. 8 and moving into the arrangement of FIG. 9.

Figure 9:
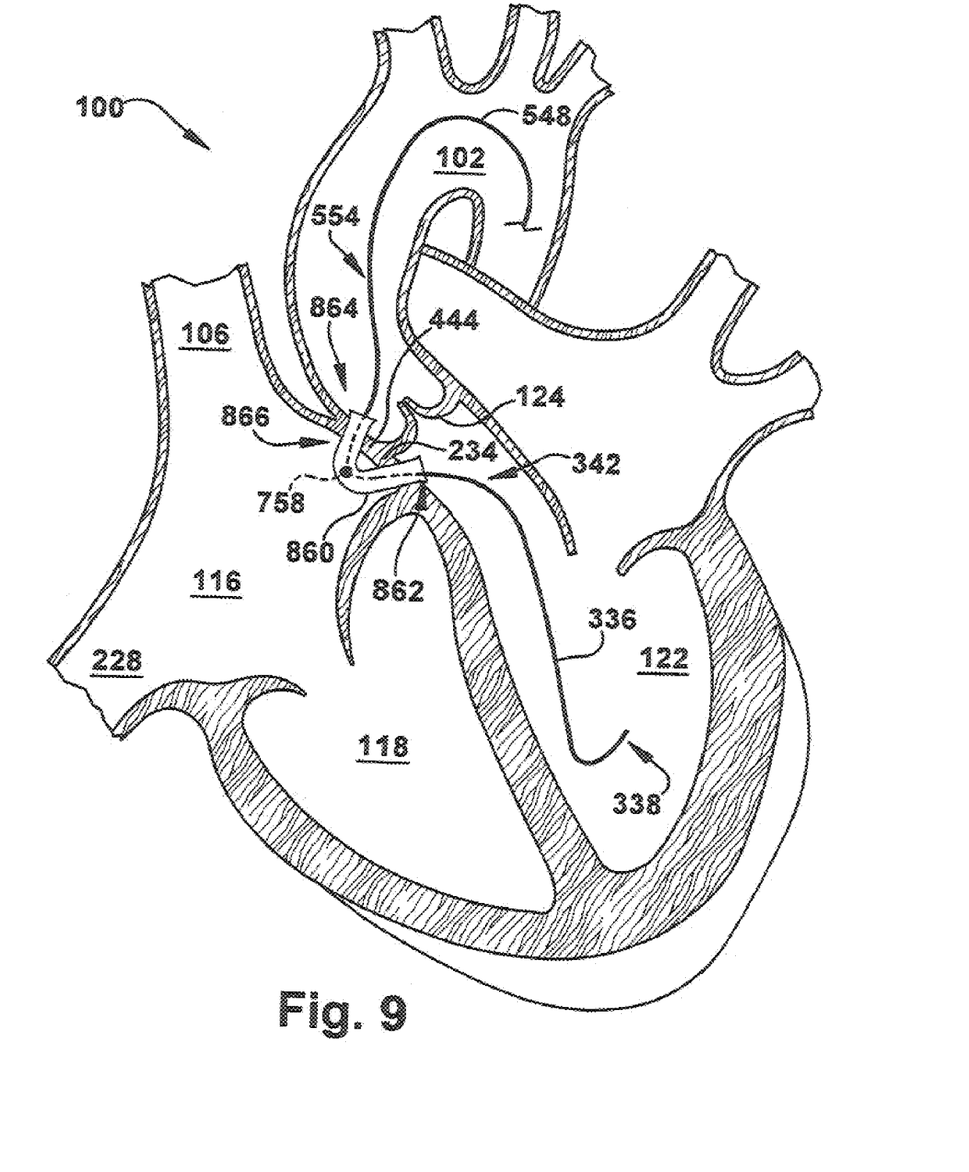

The conduit 860 depicted in FIG. 9 is in a final installation location, with the first conduit end 862 in fluid communication with the left ventricle 122, the second conduit end 864 in fluid communication with the ascending aorta 102, and the conduit body 866 extending through the right atrium 116. When the guidewire junction 758 is in the right atrium 116, the conduit body 866 surrounds the guidewire junction. In order to reach this location, at least a portion of the conduit 860 must pass through the atrioventricular septum 234. The first and second conduit ends 862 and 864 may now be anchored in the left ventricle 122 and ascending aorta 102, respectively, in any suitable manner such as, but not limited to, frictional interference, a mechanical connection, adhesion, or the like. For example, the first and second conduit ends 862 and 864 may be flared, as shown, once the conduit 860 is arranged as in FIG. 9, to prevent the first and second conduit ends from pulling through the atrioventricular septum 234 and wall 444 of the ascending aorta 102 and into the right atrium 116. A suture, staple, or the like (not shown) may assist in holding the first and second conduit ends 862 and 864 in their respective anchored positions, regardless of any other anchoring structures or methods that may be used.

Once the conduit 860 is anchored in the desired location within the heart 100, the first and second guidewires 336 and 548 may be withdrawn from the heart. Since the distal second guidewire end 550 is accessible from outside the patient's body in the arrangement of FIG. 9, the linked first and second guidewires 336 and 548 may be withdrawn from the heart 100 by being advanced through the ascending aorta 102 and out of the body in a known manner.

Figure 10:
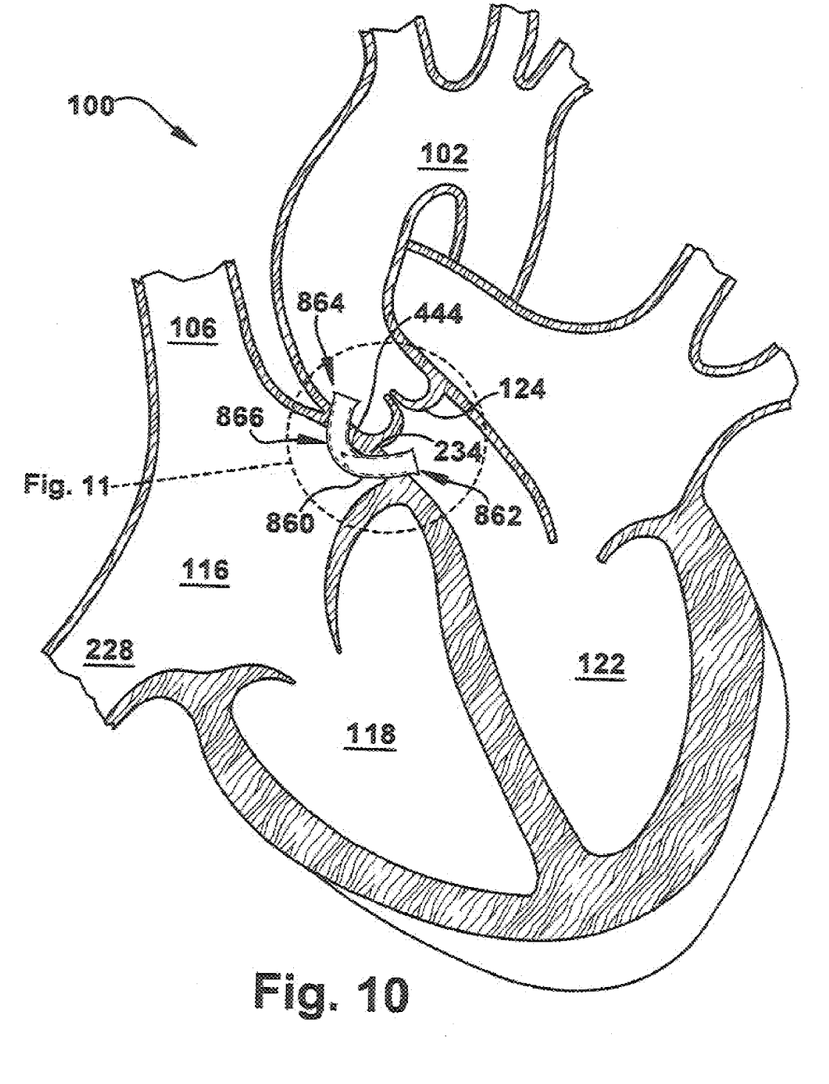
Figure 11:
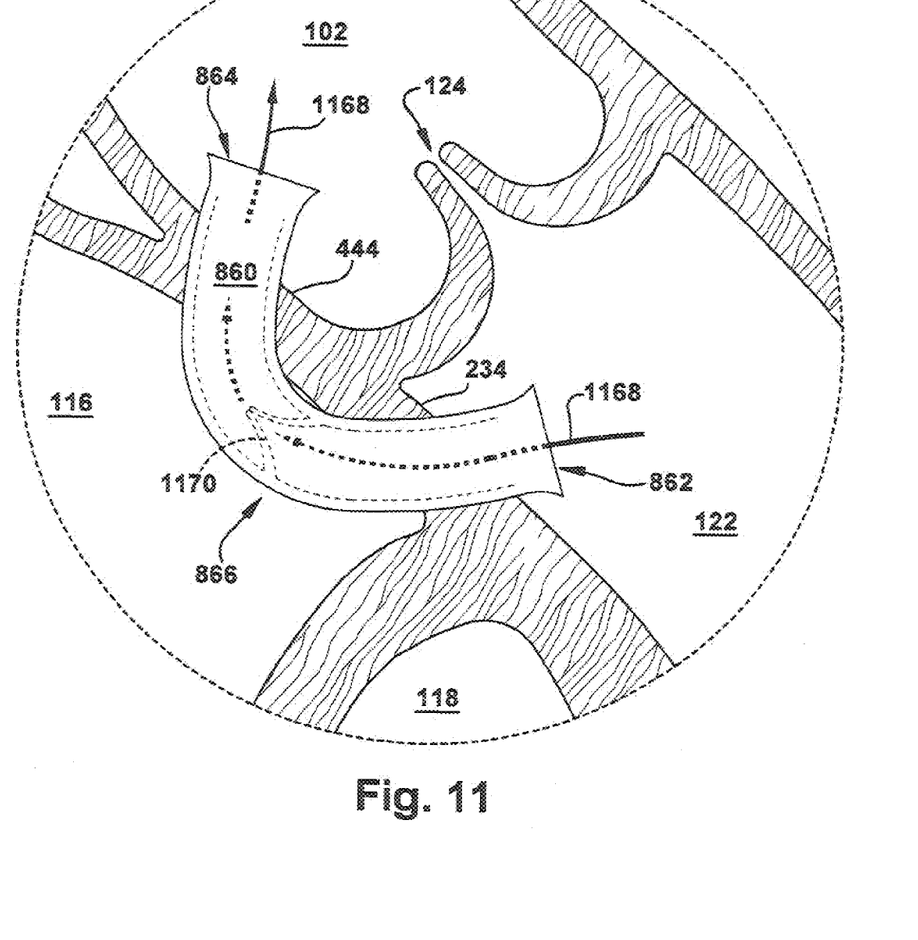
FIG. 11 is a partial schematic anterior view of the circled area "11" in FIG. 9, depicting the embodiment of FIGS. 2-10.

Upon withdrawal of the first and second guidewires 336 and 548 from the body, installation of the now-anchored conduit 860 is complete, as shown in FIG. 10. The first and second conduit ends 862 and 864 are anchored in the left ventricle 122 and ascending aorta 102, respectively, with the conduit body 866 extending through the right atrium 116 to provide the artificial fluid flow path, shown by arrows 1168 of FIG. 11. The artificial fluid flow path 1168 at least partially bypasses the native aortic valve 124. Instead of disturbing the native aortic valve 124, the artificial fluid flow path 1168 provides an alternate route for blood to leave the left ventricle 122. Thus, a problematic native aortic valve 124 can remain undisturbed and in place, while the artificial fluid flow path 1168 helps the heart 100 supply adequate blood to the rest of the patient's body. Since the native aortic valve 124 is not disturbed, the present invention helps the surgeon avoid releasing stenotic debris into the patient's cardiovascular system. In addition, the native aortic valve 124 remains in a natural condition and may be addressed for the first time in later, possibly more complex, surgeries as indicated for the patient, without the later surgeries having to take into account any changes made to the native aortic valve by the method of the present invention.

Because the conduit 860 places the left ventricle 122 into direct fluid communication with the ascending aorta 102, as previously described, it may be desirable to selectively regulate fluid communication through the artificial fluid flow path 1168, to preserve natural rhythms and operation of the heart 100. To this end, an artificial aortic valve 1170 of any suitable type is optionally located within the conduit body 866, as shown in phantom line in FIG. 11. This artificial aortic valve 1170, when present, may supplement or supplant the native aortic valve 124.

The method and apparatus shown and described above utilize a compound guidewire, formed from the linkage of the first and second guidewires 336 and 548 at the guidewire junction 758. However, a unitary guidewire (not shown) could instead be used in the present invention. Rather than undergo the positioning and linking procedure of FIGS. 2-6 and the corresponding text, the unitary guidewire, when present, could be arranged within the patient's body with a distal unitary guidewire end in the left ventricle 122 of the heart 100, the proximal unitary guidewire end in the ascending aorta 102 or downstream thereof, and a unitary guidewire body extending longitudinally between the distal and proximal guidewire ends. The unitary guidewire body would then be located at least partially in the right atrium 116 of the heart 100.

The net effect of a unitary guidewire arrangement, therefore, would be to provide a substantially similar guidewire path to that shown in FIG. 7 by the compound guidewire formed from the linkage of the independently inserted first and second guidewires 336 and 548 at the guidewire junction 758. The conduit 860 could then be advanced over the unitary guidewire, when present, and installed within the heart 100 similarly to the described method of FIGS. 8-11 and the corresponding text, with the exception of slightly different terminology for the free ends of the unitary guidewire than for the corresponding free ends of the compound guidewire. That is, the conduit 860 would be advanced along the unitary guidewire from a chosen one of the proximal and distal unitary guidewire ends toward the other one of the proximal and distal unitary guidewire ends. Other than that semantic difference, the unitary guidewire, when provided, would function similarly to the above-described compound guidewire arrangement in substantially every way except the method of positioning of each unitary or compound guidewire into the arrangement of FIG. 7 within the heart 100.

It is contemplated that the conduit 860 described above could be placed into the depicted and described position in a manner other than that illustrated. For example, the conduit 860 could be arranged within the heart 100 in an open-heart surgical procedure, or a different arrangement or series of guidewires could be used than that depicted. However, any alternate installation arrangement can be readily seen by one of ordinary skill in the art to fall under the scope of the present invention.

Once the linkage process is complete and the first and second guidewires 336 and 548 are positioned in a desired manner, the guidewire junction 758 may be located in the right atrium 116, as shown in FIG. 7. When the guidewire junction 758 remains in the right atrium, the conduit body 866 will surround the guidewire junction once the conduit 860 has reached the terminal position of FIGS. 10 and 11.

Alternately, and not shown, the guidewire junction 758 may be located in the left ventricle 122, the ascending aorta 102, or downstream of the ascending aorta. For example, once the first and second guidewires 336 and 548 are linked at the proximal first and second guidewire ends 340 and 552, the distal second guidewire end 232 may be advanced further in the caudad direction 656, to the extent that the guidewire junction 758 (and attached proximal first guidewire end) are pulled through the wall 444 of the ascending aorta 102, through the ascending aorta itself, or to a location even further downstream of the heart 100.

It is contemplated that, with an appropriate choice of length for the first guidewire 336, the second guidewire 548 could even exit the patient's body completely, resulting in the first guidewire 336 extending from the left ventricle 122 all the way through the ascending aorta 102 and out of the patient's body. If this arrangement is created, the first guidewire 336 will function as would a unitary guidewire (as described above), with the conduit 866 being advanced from the proximal first guidewire end 340 (now extending outside the patient's body) toward the distal first guidewire end 338 (located in the left ventricle 122).

The conduit body 866 may be made of a partially permeable or non-permeable material. It is also contemplated that the conduit 866 or any portion thereof may be adapted to elute a therapeutic agent, such as, but not limited to, an anesthetic, anti-inflammatory, or antiseptic agent, to the heart 100. "Elute" is used herein to indicate that a therapeutic agent is released, leached, diffused, or otherwise provided to the target tissue.

The native aortic valve 124 may be at least partially occluded, either congenitally or by natural or artificial acquisition. For example, the native aortic valve 124 may have become stenotic in a natural process or may be held closed by a clip, suture, or other artificial means.

It is also contemplated that the distal introduction catheter end 232' could exit the heart 100 through any wall of the right atrium 116 and approach the ascending aorta 102 from outside the heart 100. Also or instead, the aortic access area 146 may be located in lateral alignment with at least one of the left and right coronary arteries 110 and 108 (i.e., offset from at least one of the left and right coronary arteries around a circumference of the ascending aorta 102, the circumference linking the left and right coronary arteries). One of ordinary skill in the art can readily choose a location for the aortic access area 146 responsive to one or more of equipment limitations, patient particularities, surgeon preferences, or the like.

While aspects of the present invention have been particularly shown and described with reference to the preferred embodiment above, it will be understood by those of ordinary skill in the art that various additional embodiments may be contemplated without departing from the spirit and scope of the present invention. For example, a similar method and/or apparatus could be used to supplement or bypass any heart valve, through any wall or septum of the heart or adjacent body structures. An additional guidewire, catheter, or other endovascular device could be used to advance the conduit 860 into the heart 100. The distal first guidewire end 338, or another portion of the first guidewire 336, may include a feature which at least partially anchors the first and second conduit ends 862 and 863 when the first guidewire 336 is withdrawn from the heart 100 through the installed conduit 860. The steps described above may be carried out in any suitable order. Any of the above-described structures could be made of any material, using any process, and may have any desired shapes, sizes, orientations, and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. A method of placing a left ventricle outflow tract of a patient's heart into fluid communication with an ascending aorta through an artificial fluid flow path, the method comprising the steps of:

arranging a guidewire within a patient's body, the guidewire being a compound guidewire having proximal and distal compound guidewire ends longitudinally spaced by a compound guidewire body, the distal guidewire end being arranged in a left ventricle of the heart, the proximal guidewire end being arranged in the ascending aorta, and the guidewire body, extending longitudinally between the distal and proximal guidewire ends, located at least partially in a right atrium of the heart, the arrangement of the guidewire within the patient's body including the steps of independently inserting first and second guidewires into the patient's body, the first guidewire having distal and proximal first guidewire ends longitudinally spaced by a first guidewire body, and the second guidewire having distal and proximal second guidewire ends longitudinally spaced by a second guidewire body, and forming the compound guidewire from first and second guidewires by linking the proximal first and second guidewire ends to form at least a portion of the compound guidewire body, the distal first guidewire end functioning as the distal compound guidewire end and the distal second guidewire end functioning as the proximal compound guidewire end;

providing a conduit having longitudinally spaced first and second conduit ends in mutual fluid communication through a tubular conduit body;

advancing the conduit along the guidewire from a chosen one of the proximal and distal guidewire ends toward the other one of the proximal and distal guidewire ends;

anchoring the first conduit end in the left ventricle; and anchoring the second conduit end in the ascending aorta to provide the artificial fluid flow path.

2. The method of claim 1, wherein the step of advancing the conduit along the guidewire from a chosen one of the proximal and distal guidewire ends toward the other one of the proximal and distal guidewire ends includes the step of passing at least a portion of the conduit through an atrioventricular septum of the heart.

3. The method of claim 1, including the steps of:

routing the distal first guidewire end through a right atrium of the heart into a left ventricle of the heart;

routing the distal second guidewire end through the right atrium into the ascending aorta;

advancing the distal second guidewire end caudad to the patient; and linking the proximal first guidewire end and the proximal second guidewire end at a guidewire junction to form the compound guidewire, the linked proximal first and second guidewire ends and the guidewire junction becoming part of the compound guidewire body.

4. The method of claim 1, wherein the conduit includes an artificial aortic valve located within the conduit body, the artificial aortic valve being adapted to selectively permit fluid communication through the artificial fluid flow path.

* * * * *